United States Patent [19]

Sauer et al.

[11] Patent Number: 5,690,664
[45] Date of Patent: Nov. 25, 1997

[54] TROCAR HAVING MOVABLE BLADE

[75] Inventors: Jude S. Sauer; Alexander I. Kobilansky, both of Pittsford, N.Y.; Marc J. Theroux, Bethel, Conn.; Carl T. Urban, Lake Oswego, Oreg.

[73] Assignee: United States Surgical Corporation, Norwalk, Conn.

[21] Appl. No.: 715,305

[22] Filed: Sep. 18, 1996

Related U.S. Application Data

[63] Continuation of Ser. No. 322,884, Oct. 13, 1994, abandoned, which is a continuation-in-part of Ser. No. 249,707, May 26, 1994, which is a continuation-in-part of Ser. No. 132,403, Oct. 6, 1993, Pat. No. 5,467,762, which is a continuation-in-part of Ser. No. 120,489, Sep. 13, 1993, Pat. No. 5,441,041.

[51] Int. Cl.$^6$ .................................................. A61B 17/34
[52] U.S. Cl. ........................ 606/185; 606/167; 604/164
[58] Field of Search ............................ 604/164, 264, 604/172, 272; 606/167, 181, 182, 183, 184, 185

[56] References Cited

U.S. PATENT DOCUMENTS

| | | |
|---|---|---|
| 1,380,447 | 6/1921 | Wescott . |
| 2,699,770 | 1/1955 | Fourestier et al. . |
| 3,538,916 | 11/1970 | Wiles . |
| 3,762,416 | 10/1973 | Moss et al. . |
| 3,809,095 | 5/1974 | Cimber . |
| 3,915,169 | 10/1975 | McGuire . |
| 4,210,146 | 7/1980 | Banko . |
| 4,220,155 | 9/1980 | Kimberling et al. . |
| 4,254,762 | 3/1981 | Yoon . |
| 4,256,119 | 3/1981 | Gauthier . |
| 4,411,653 | 10/1983 | Razi ........................ 604/157 |
| 4,461,305 | 7/1984 | Cibley . |
| 4,516,575 | 5/1985 | Gerhard et al. . |
| 4,539,976 | 9/1985 | Sharpe . |
| 4,559,041 | 12/1985 | Razi . |
| 4,570,632 | 2/1986 | Woods . |
| 4,601,710 | 7/1986 | Moll ........................ 604/165 |
| 4,653,475 | 3/1987 | Seike et al. . |
| 4,667,684 | 5/1987 | Leigh . |
| 4,723,545 | 2/1988 | Nixon et al. . |
| 4,733,671 | 3/1988 | Mehl . |
| 4,790,312 | 12/1988 | Capuano, Sr. . |
| 4,957,112 | 9/1990 | Yokoi et al. . |
| 4,962,770 | 10/1990 | Agee et al. . |
| 4,976,269 | 12/1990 | Mehl ........................ 128/754 |
| 4,991,600 | 2/1991 | Taylor . |
| 5,066,288 | 11/1991 | Deniega et al. ........ 604/274 |
| 5,089,000 | 2/1992 | Agee et al. ............. 606/170 |
| 5,092,872 | 3/1992 | Segalowitz ............. 606/159 |
| 5,104,382 | 4/1992 | Brinkerhoff et al. ... 604/165 |
| 5,116,353 | 5/1992 | Green ..................... 606/184 |
| 5,146,921 | 9/1992 | Terwilliger et al. .... 128/754 |
| 5,152,754 | 10/1992 | Plyley et al. ........... 604/164 |
| 5,158,552 | 10/1992 | Borgia et al. .......... 604/165 |
| 5,176,695 | 1/1993 | Dulebohn ............... 606/170 |
| 5,183,053 | 2/1993 | Yeh et al. ............... 128/754 |
| 5,186,178 | 2/1993 | Yeh et al. ............... 128/754 |
| 5,275,583 | 1/1994 | Crainich ................. 604/264 |
| 5,314,417 | 5/1994 | Stephens et al. ....... 604/264 |
| 5,354,302 | 10/1994 | Ko ........................... 606/104 |
| 5,372,588 | 12/1994 | Farley et al. ........... 604/164 |
| 5,385,572 | 1/1995 | Nobles et al. .......... 606/185 |
| 5,406,940 | 4/1995 | Melzer et al. . |

FOREIGN PATENT DOCUMENTS

| | | |
|---|---|---|
| 9112976 | 12/1991 | Germany . |
| 537677 | 12/1976 | U.S.S.R. . |

*Primary Examiner*—Michael Buiz
*Assistant Examiner*—Patrick W. Rasche

[57] ABSTRACT

A surgical apparatus is provided for penetrating body tissue. The apparatus includes a cannula and an obturator configured for insertion into the cannula. The obturator has a body tissue cutting member mounted to a distal portion which is movable between deployed and non-deployed positions. An actuating mechanism is operatively associated with the tissue cutting member and is selectively controllable by a user so as to move the tissue cutting member between the deployed and non-deployed positions independent of the position of the obturator.

22 Claims, 13 Drawing Sheets

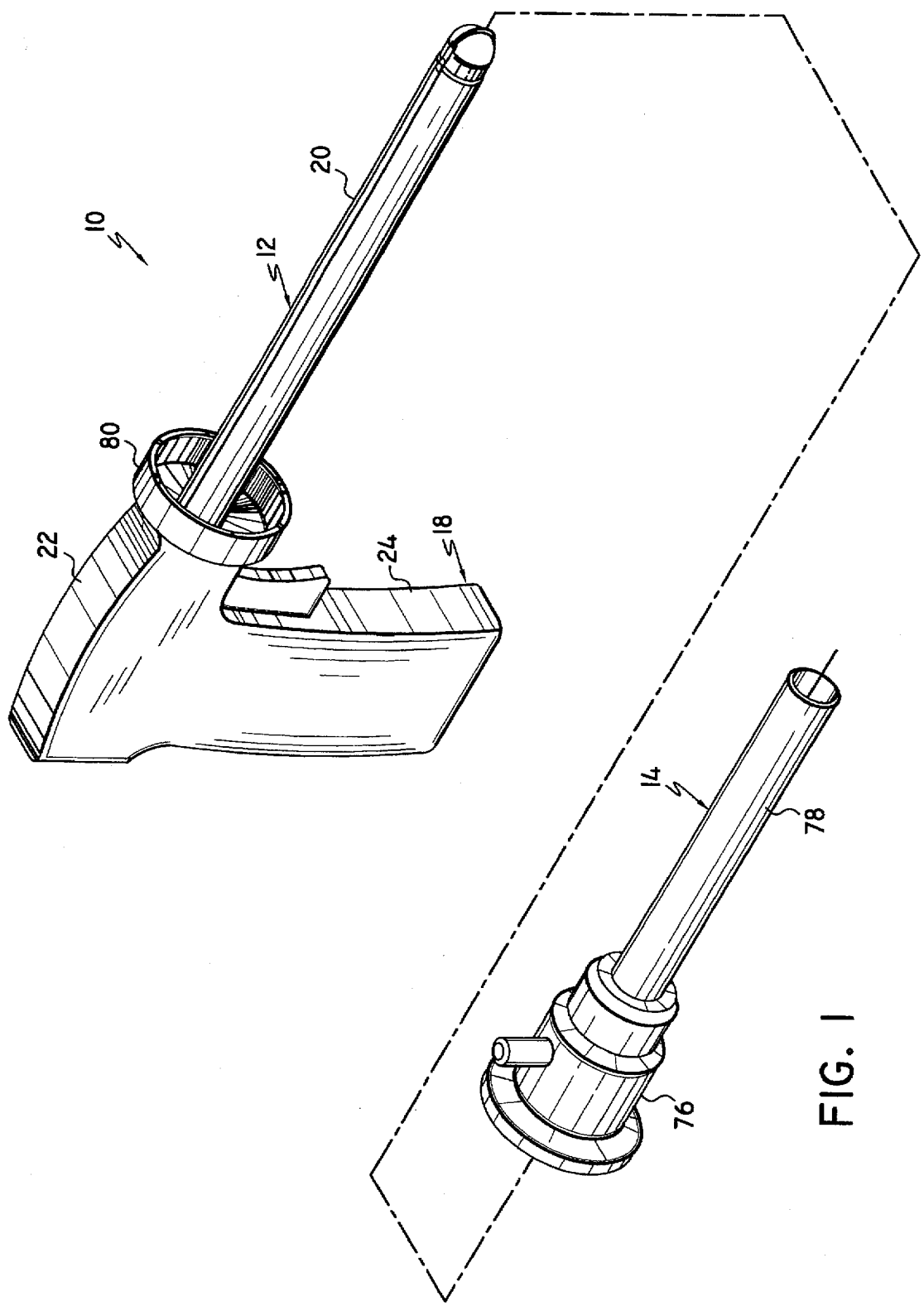

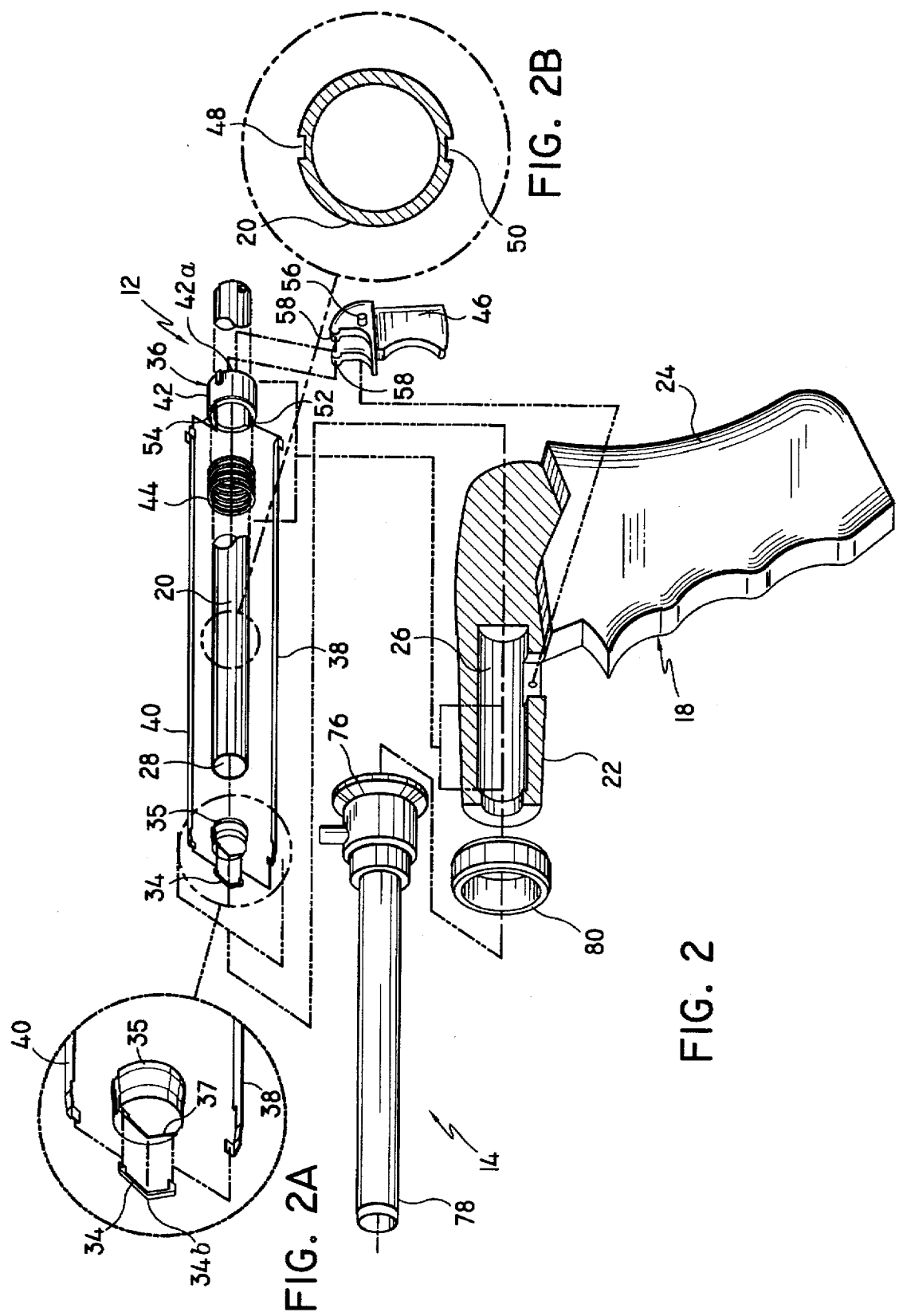

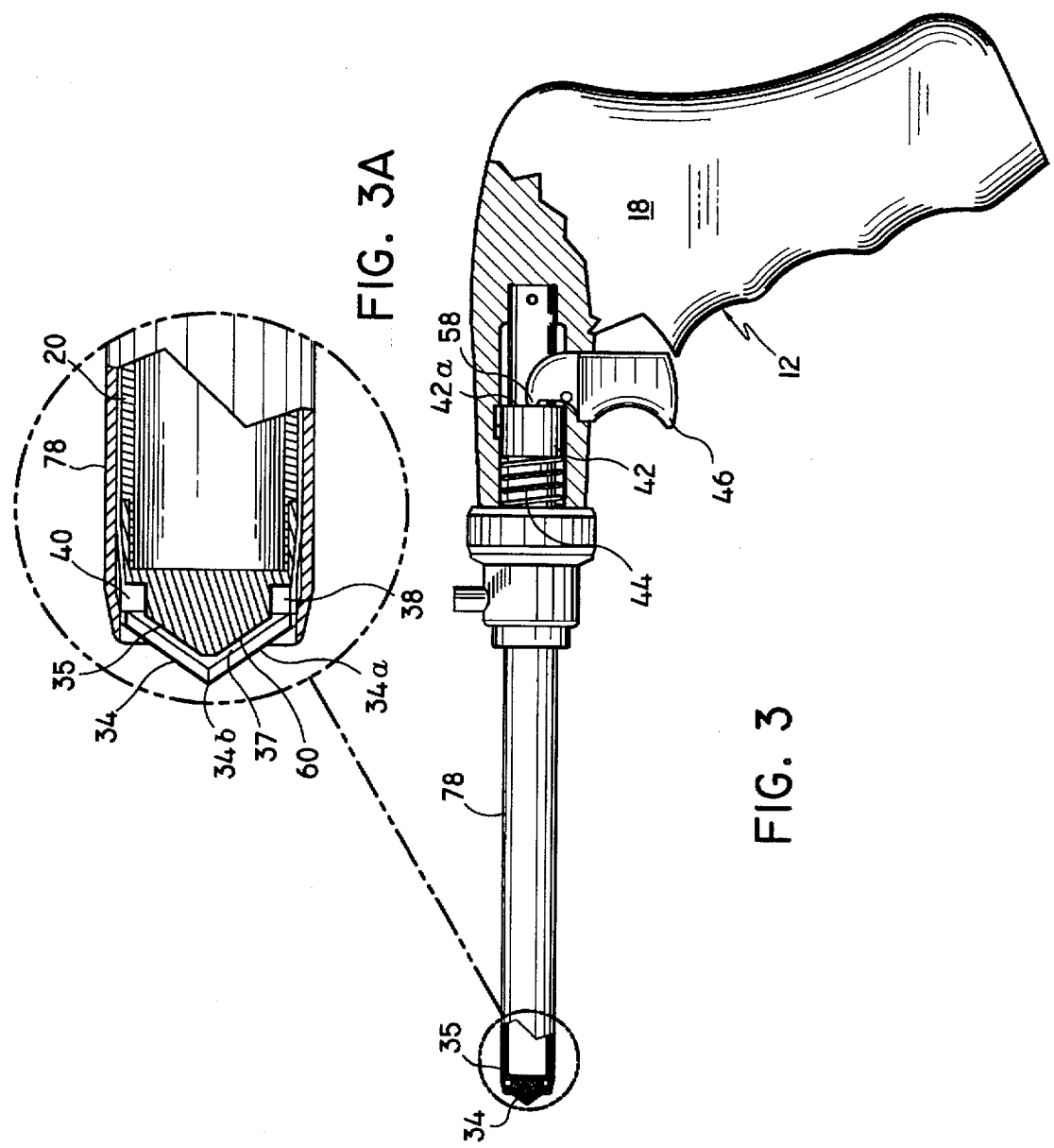

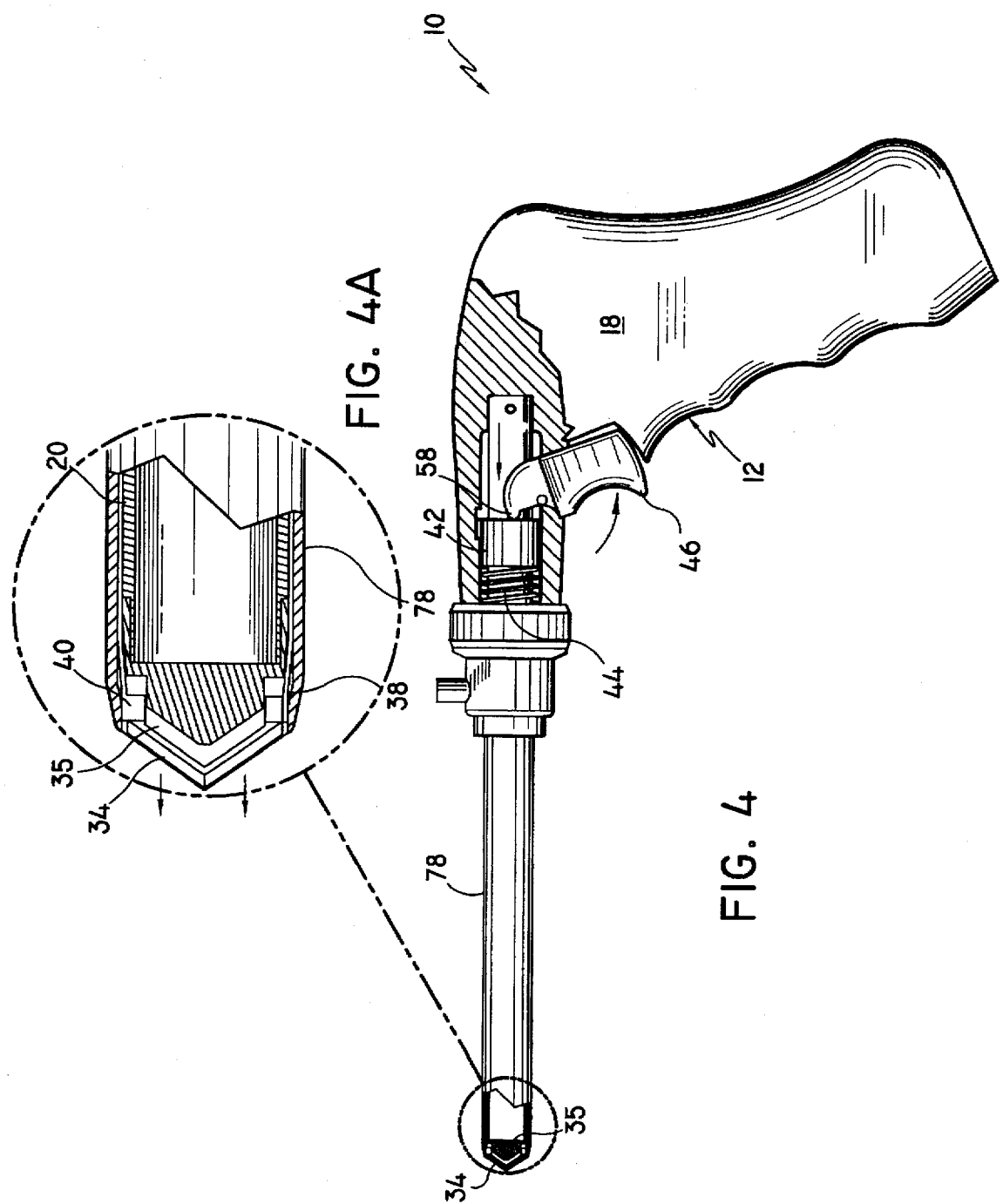

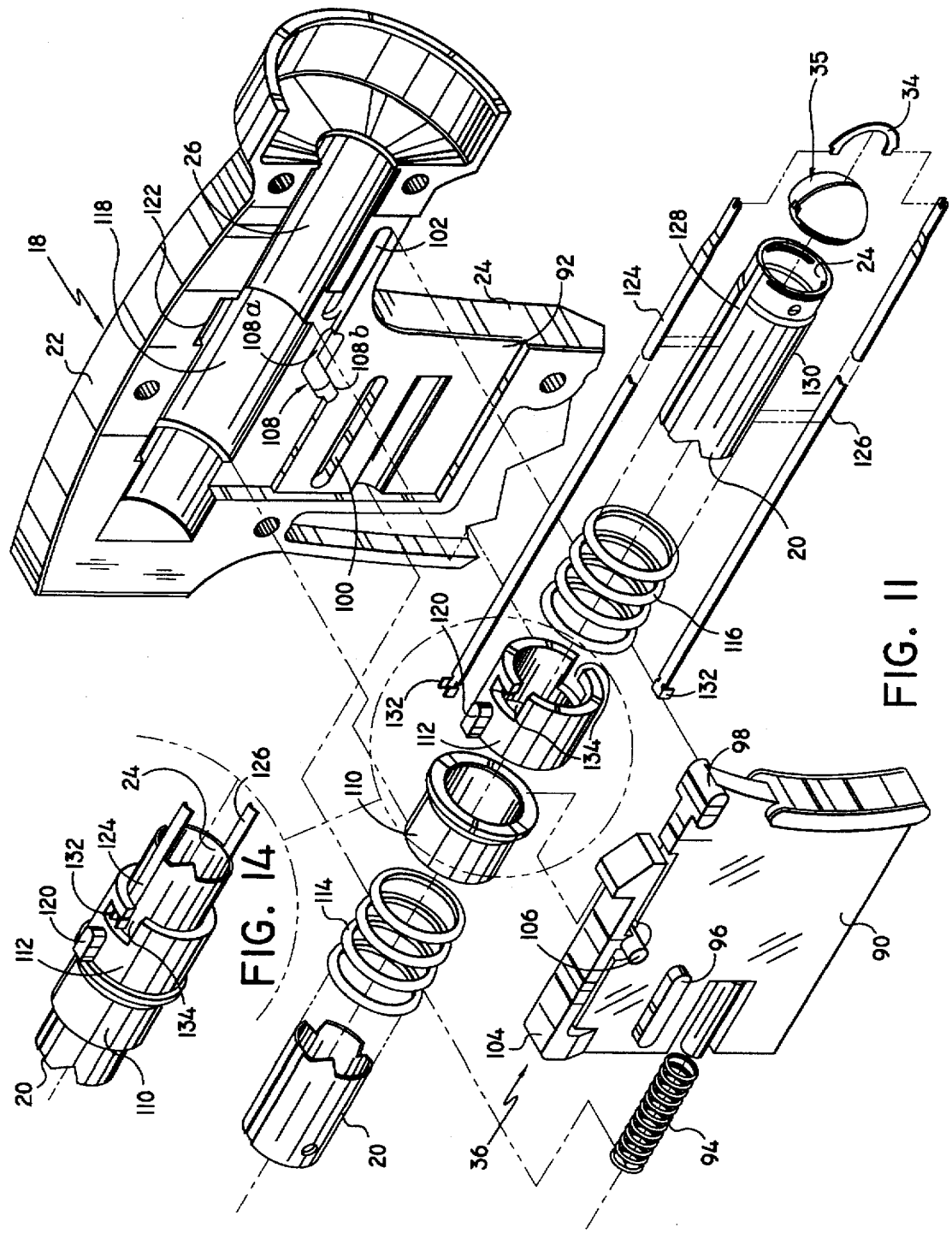

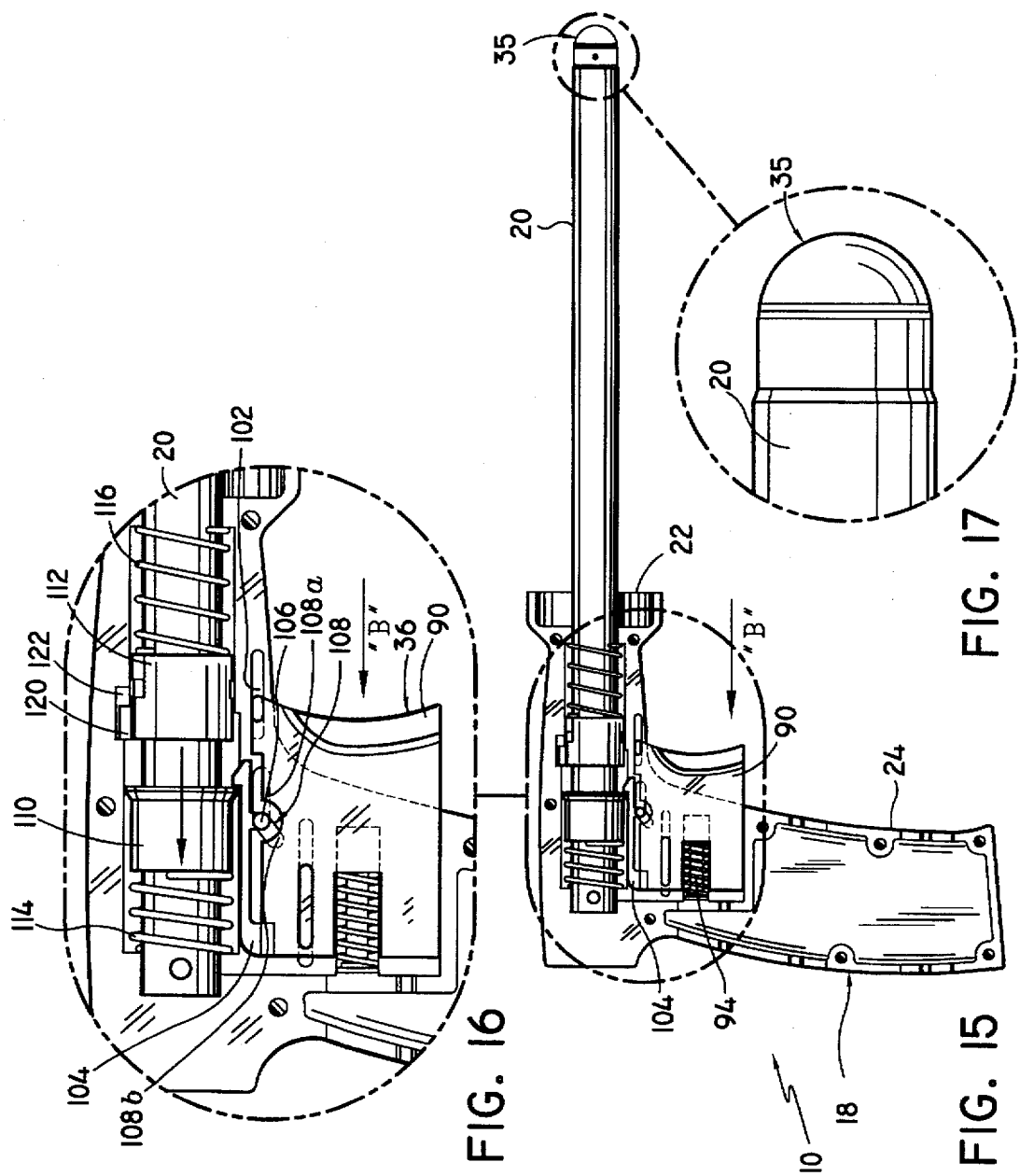

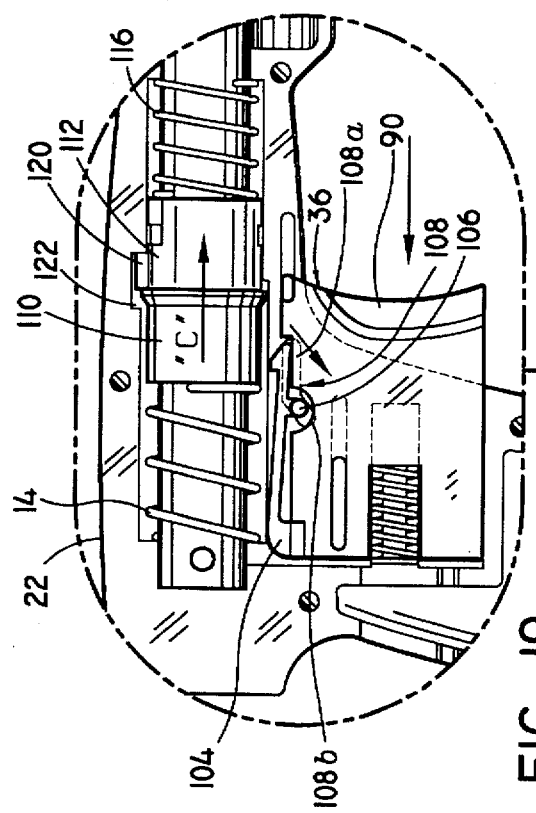
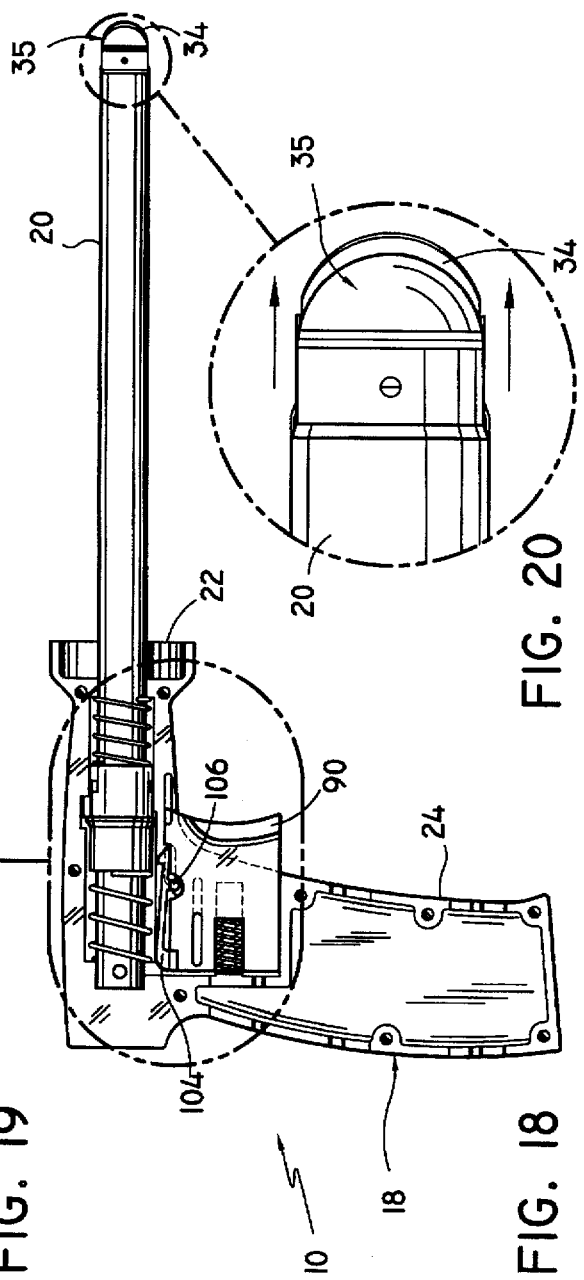
FIG. 19
FIG. 20
FIG. 18

TROCAR HAVING MOVABLE BLADE

CROSS-REFERENCE TO RELATED APPLICATIONS

This is a continuation of application Ser. No. 08/322,884, filed on Oct. 13, 1994, now abandoned which is a continuation-in-part of U.S. application Ser. No. 08/249,707, filed May 26, 1994, which is a continuation-in-part of U.S. application Ser. No. 08/132,403, filed Oct. 6, 1993, now U.S. Pat. No. 5,467,762 issued Nov. 21, 1995, which is a continuation-in-part of U.S. application Ser. No. 08/120,489, filed Sep. 13, 1993 now U.S. Pat. No. 5,441,041, issued Aug. 15, 1995.

BACKGROUND

1. Technical Field

A trocar assembly having a movable blade for penetrating body tissue is provided. More particularly, the trocar assembly has a reciprocating blade which may be selectively deployed to penetrate the peritoneum or other body tissue.

2. Description of Related Art

Endoscopic and laparoscopic surgical procedures, that is, surgical procedures performed through tubular sleeves or cannulas, have been utilized for many years. In endoscopic procedures, surgery is performed in any hollow viscus of the body through a small incision or through narrow endoscopic tubes (cannulas) inserted through small entrance wounds in the skin. In laparoscopic procedures surgery is performed in the interior of the abdomen. Initially, such surgical procedures were primarily diagnostic in nature. More recently, endoscopic and laparoscopic surgical techniques and instrumentation have advanced to permit surgeons to perform increasingly complex and innovative surgical procedures.

Endoscopic and laparoscopic procedures often require the surgeon to act on organs, tissues and vessels far removed from the incision, thereby requiring that any instruments to be used in such procedures be of sufficient size and length to permit remote operation. Moreover, such procedures generally utilize instrumentation that is internally sealed to inhibit gases from entering or exiting the body through the laparoscopic or endoscopic incision. This is particularly true in surgical procedures in which the surgical region is insufflated.

Typically, after the surgical region is insufflated, trocars are used to puncture the body cavity and include a cannula which remains in place for use during the endoscopic or laparoscopic procedures. Heretofore, trocars used during such procedures include a protective tube and a styler having a sharp tip which is positioned coaxially within the protective tube to protect a patient or surgeon from inadvertent contact with the tip. An example of a known trocar is described in commonly assigned, U.S. Pat. No. 4,601,710 to Moll. Most currently used trocars require the surgeon to apply pressure to the trocar to cause the sharp tip to penetrate the body tissue. The amount of pressure required often varies depending on, for example, the thickness of the tissue being penetrated.

The trocar assembly of the present invention provides an alternative technique for penetrating the body tissue by providing a reciprocating blade to incise body tissue while the trocar penetrates the body tissue.

SUMMARY

A surgical apparatus for penetrating body tissue is disclosed. In particular, a trocar assembly is provided having a movable blade at a distal end portion which cuts or severs the body tissue during penetration. The trocar assembly includes a cannula, an obturator having a proximal portion and a distal portion and which is configured for insertion into the cannula. A body tissue cutting member is mounted to the distal portion of the obturator and is movable between deployed and non-deployed positions. An actuating mechanism is also provided to move the tissue cutting member between the deployed and non-deployed positions independent of the position of the obturator.

In one embodiment, the actuating mechanism includes a pair of pusher members each having a proximal portion connected to a drive mechanism and a distal portion connected to the tissue cutting member. A trigger is operatively connected to the drive mechanism for longitudinally moving the pair of pusher members. The pair of pusher members are associated with the obturator and longitudinally movable relative to the obturator.

To achieve the longitudinal movement of the pusher members, the trigger may be pivotally mounted to an obturator housing such that pivotal movement of the trigger is translated to longitudinal movement of the pusher members. In an alternative embodiment, the trigger is movable between first and second predetermined positions such that movement of the trigger to the first predetermined position causes the pusher members to move the tissue cutting member to the deployed position, and movement of the trigger to the second position causes the at least one pusher member to move the tissue cutting member to the non-deployed position.

Generally, the tissue cutting member is positioned within a recess in the obturator when in the non-deployed position and extends from the obturator when deployed. Alternatively, a housing may be positioned at the distal portion of the obturator to receive the tissue cutting member when in the non-deployed position. Preferably, the tissue cutting member is a blade having an apex. However, other blade configurations are contemplated, such as an arcuate shaped blade.

BRIEF DESCRIPTION OF THE DRAWINGS

Preferred embodiments are described hereinbelow with reference to the drawings wherein:

FIG. 1 is a perspective view with parts separated of a trocar assembly with a movable blade;

FIG. 2 is a side elevational view with parts separated of the trocar assembly with a movable blade;

FIG. 2A is an enlarged perspective view of the movable cutting blade and a blade housing;

FIG. 2B is an enlarged cross-sectional view of an obturator sleeve shown in FIG. 2;

FIG. 3 is a side elevational view in partial cross-section of the trocar assembly of FIG. 2, illustrating the cutting blade in the non-deployed position within the blade housing;

FIG. 3A is an enlarged partial cross-sectional view of the distal end of the trocar assembly of FIG. 3, illustrating the cutting blade recessed within the blade housing;

FIG. 4 is a side elevational view in partial cross-section of the trocar assembly of FIG. 2, illustrating the cutting blade in the deployed position;

FIG. 4A is an enlarged partial cross-sectional view of the distal end of the trocar assembly of FIG. 4, illustrating the cutting blade extending from the blade housing;

FIG. 11 is a perspective view with parts separated of a portion of an alternative embodiment of the blade actuating mechanism;

FIG. 14 is a sectional assembled view of a portion of the blade actuating mechanism of FIG. 11, illustrating the interconnection of the blade pusher arms to the actuating mechanism;

FIG. 15 is a side elevational view the obturator assembly of FIG. 11, illustrating partial actuation of the blade actuating mechanism with the blade in the non-deployed position;

FIG. 16 is an enlarged side elevational view of the blade actuating mechanism of FIG. 15;

FIG. 17 is an enlarged view of the distal end of the obturator assembly of FIG. 15, illustrating the dome-shaped blade housing;

FIG. 18 is a side elevational view of the obturator assembly of FIG. 11, illustrating actuation of the blade actuating mechanism and the blade in the deployed position;

FIG. 19 is an enlarged side elevational view of the blade actuating mechanism of FIG. 18; and FIG. 20 is an enlarged view of the distal end of the obturator assembly of FIG. 18, illustrating the dome-shaped blade housing and the blade in the deployed position.

DETAILED DESCRIPTION OF PREFERRED EMBODIMENTS

Figure 3C:
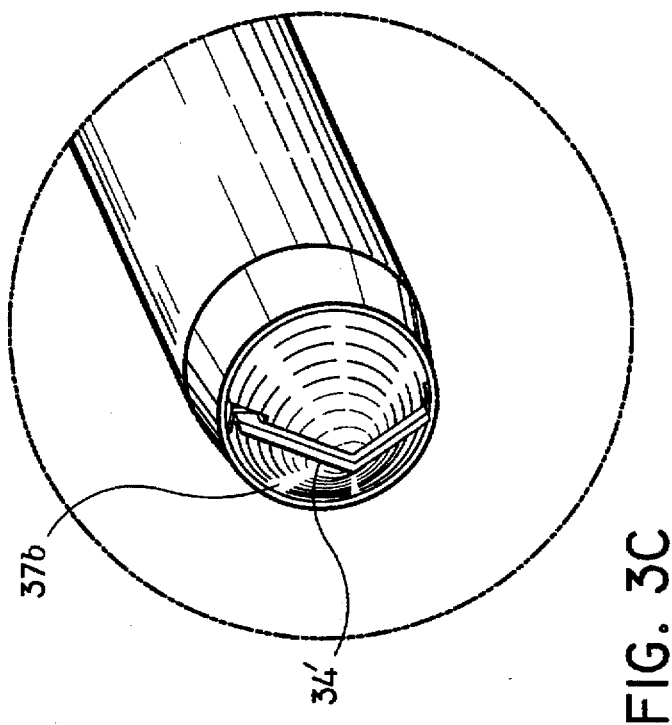
FIG. 3C is an enlarged view showing an alternate embodiment of the distal end of the trocar assembly.

The trocar assembly described herein is provided to reduce the pressure required to penetrate body tissue during endoscopic and laparoscopic surgical procedures. FIG. 1 illustrates a trocar assembly 10 which typically includes two subassemblies, an obturator assembly 12 and a cannula assembly 14. The obturator assembly and the cannula are configured to interfit during penetration and to be separated once penetration is completed. The term obturator assembly as used herein refers to the tissue penetrating assembly of the trocar assembly.

Referring to FIGS. 1 and 2, obturator assembly 12 includes housing 18 and a longitudinally extending obturator sleeve 20. Preferably, obturator housing 18 has two halves which are joined by adhesives or welding. The housing includes barrel portion 22 and hand grip 24. The proximal end of obturator sleeve 20 is secured within channel 26 of barrel portion 22 so that the obturator sleeve 20 extends outwardly from the obturator housing 18. Hand grip 24 is provided for manual gripping to facilitate penetration of the body tissue. Obturator sleeve 20 has a longitudinal bore 28 which extends between the proximal end and the distal end. The longitudinal bore 28 is configured and dimensioned to interact with the reciprocating blade and blade actuating assembly of the obturator assembly.

Referring to FIGS. 3 and 4, the cutting portion of obturator assembly 12 includes a cutting blade 34 connected to actuating assembly 36 and a blade housing 35. Blade housing 35 is positioned at the distal end of obturator sleeve 20 and includes recess 37 configured to receive blade 34 when the blade is in the non-deployed position. Blade housing 35 is provided to prevent inadvertent contact with the blade 34 by a user, as well as to support or stabilize the blade when the apparatus is not in use. Recess 37 extends transverse to the longitudinal axis of the obturator.

Figure 3B:
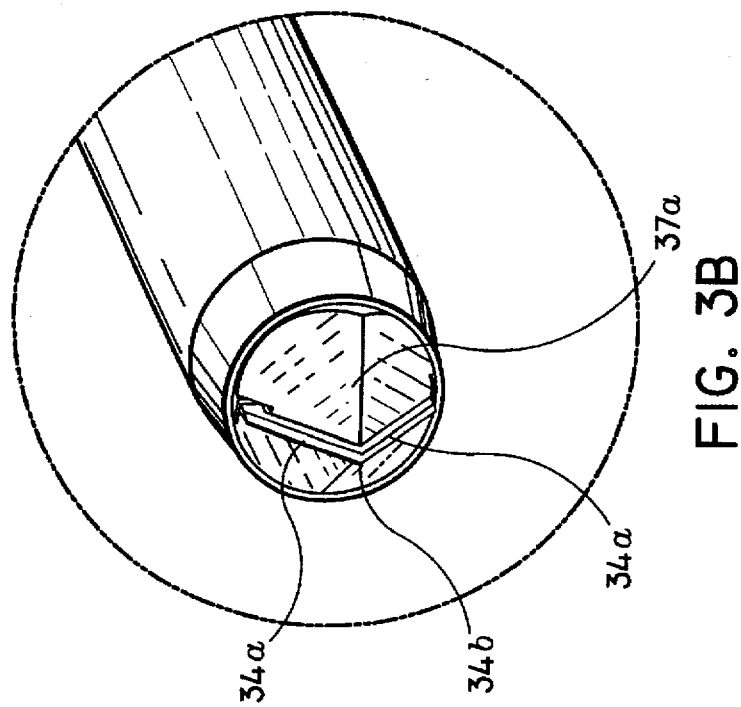
FIG. 3B is an enlarged view of the distal end of the trocar assembly illustrating the cutting blade.
Figure 6:
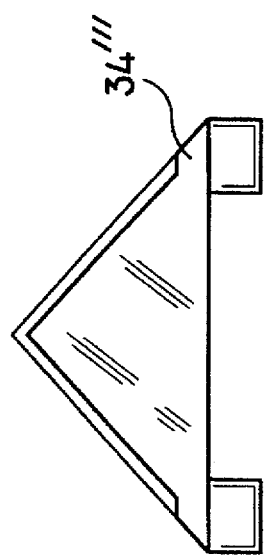
FIG. 6 is a side elevational view of another alternative embodiment of the cutting blade.
Figure 5:
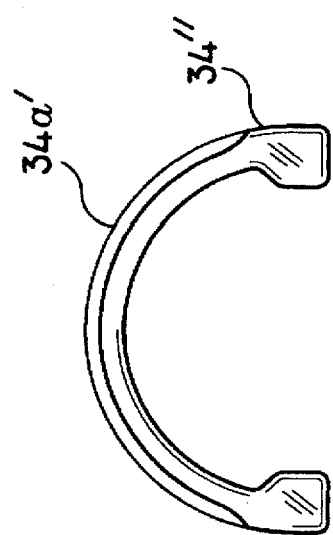
FIG. 5 is a side elevational view of an alternate embodiment of the cutting blade.

The blade extends at an angle to the longitudinal axis of the obturator. Blade 34 includes a plurality of cutting surfaces 34a which have one end joined at an apex 34b, as shown in FIGS. 3A and 3B. The cutting surfaces as shown, are two substantially straight edges angled towards each other. The blade sits in a recess 37 formed at the distal end of surface 37a which is composed of four substantially flat surfaces as shown. In the alternate embodiment of FIG. 3C, the blade 34' sits in a recess formed in conical surface 37b. The blade 34" may alternatively be arcuate in shape, as shown in FIG. 5 or the blade 34'" may be a solid triangular shape, as shown in FIG. 6. The blade may alternately be positioned in a recess formed at the distal end of the obturator itself.

Referring again to FIG. 2, actuating assembly 36 is provided to selectively control the blade 34, i.e. to move it 34 between a non-deployed position, shown in FIG. 3A, and a deployed position, shown in FIG. 4A. As is apparent, the blade moves with respect to the obturator and the actuating mechanism allows movement of the blade in any position. Consequently, movement of the blade is not dependent on the position of the obturator. In one embodiment, the actuating assembly 36 includes blade pusher arms 38 and 40, blade drive member 42, drive spring 44 and trigger 46. Blade 34 can be formed as an integral piece with blade drive member 42 and/or blade arms 38 and 40. Alternately, blade 34 can be connected, such as by welding, to the distal end of blade pusher arms 38 and 40 which extend along the longitudinal axis of obturator sleeve 20 within slots 48 and 50 in the obturator sleeve, shown in FIG. 2B. The proximal end of blade pusher arms 38 and 40 are secured within slots 52 and 54 of blade drive member 42, as shown. Blade drive member 42 and drive spring 44 are positioned within channel 26 of obturator housing 18 so that drive spring 44 normally biases blade drive member 42 toward the proximal end of obturator housing 18. As a result, blade 34 is normally biased to the proximal non-deployed position.

Trigger 46 is pivotally secured to obturator housing 18 via pin 56 so that camming surface 58 of trigger 46 engages the proximal end portion 42a of blade drive member 42. Thus, actuation of trigger 46, i.e. movement of the trigger in the direction of the arrow in FIG. 4, causes camming surface 58 to engage blade drive member 42 and move the drive member distally within channel 26. Distal movement of drive member 42 causes blade pusher arms 38 and 40 to move distally to move blade 34 distally to the deployed (extended) position. Release of trigger 46 permits blade 34 to return to the non-deployed position in response to the action of drive spring 44 forcing blade drive member 42 proximally. The blade or cutting member can also alternatively be movable in directions other than longitudinally as described above. For example, the blade can be movable in a direction transverse to the longitudinal axis, or the blade can vibrate.

The movement of blade 34 between non-deployed and deployed positions can be seen by comparing FIGS. 3A and 4A. As shown in FIG. 3A, in the non-deployed position the blade 34 is at rest within recess 37 in blade housing 35. In the deployed position blade 34 is extended from recess 37 beyond the distal end of cannula assembly 14, as shown in FIG. 4A.

An alternative embodiment of the actuating assembly 36 is shown in FIGS. 7–10. In this embodiment, an automatic release member is associated with blade drive member 42 and trigger 46 and is provided to automatically return blade 34 to the non-deployed position after the blade is deployed. That is, the blade 34 returns to its initial undeployed position without requiring release of the trigger 46.

Figure 7:
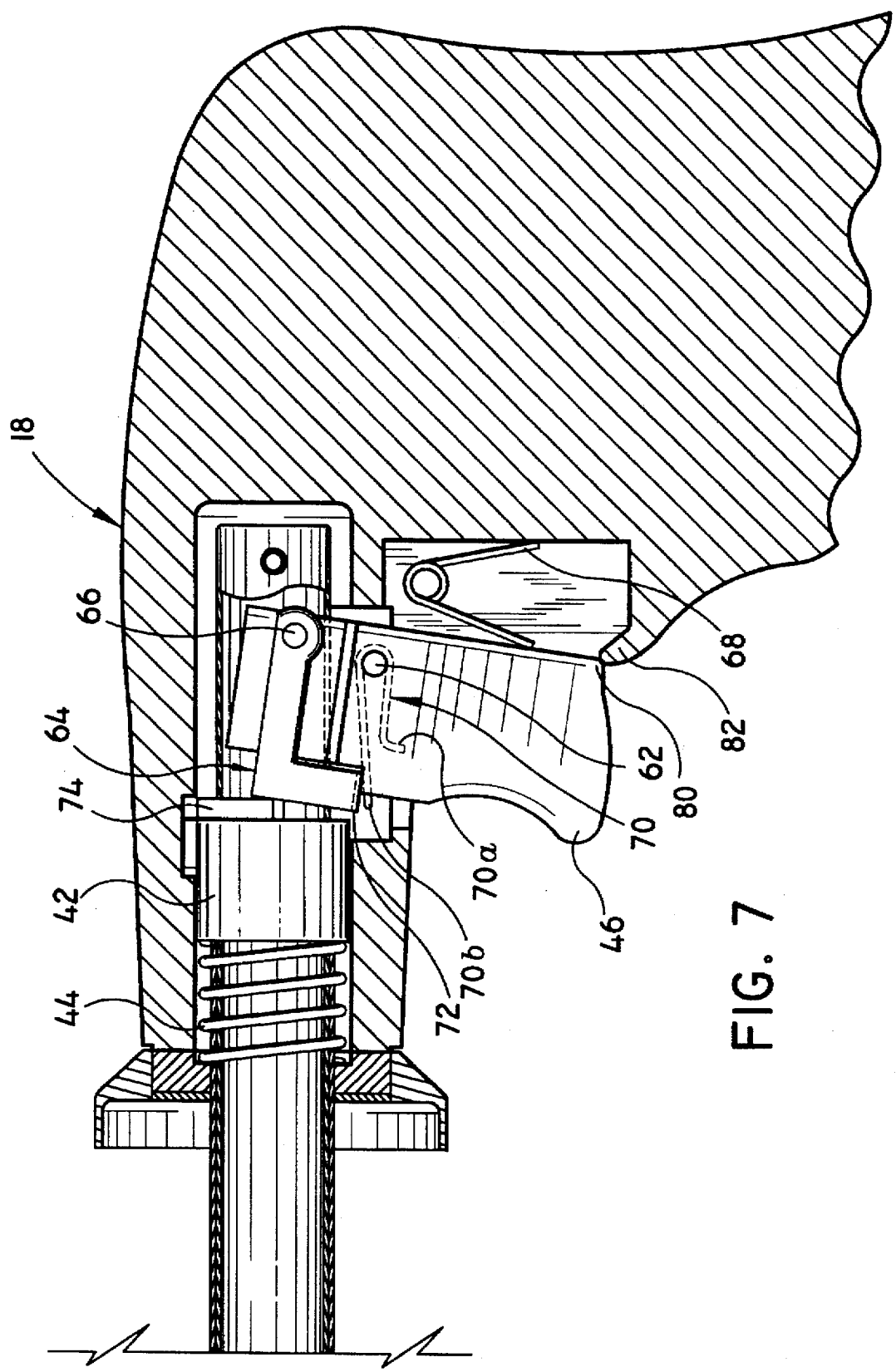
FIGS. 7, 8 and 9 are side elevational views of an alternative embodiment of the blade actuation mechanism.

Referring to FIG. 7, trigger 46 is pivotally secured to obturator housing 18 via pin 62 and lever 64 is pivotally secured to trigger 46 via lever pin 66. Spring 68 biases trigger 46 distally. Lever spring 70 is secured to trigger 46 at one end 70a and is positioned around pin 62, as shown. The biasing arm 70b of lever spring 70 engages crossbar 72 of lever 64, shown in FIG. 10, and is provided to pivot lever 64 clockwise a predetermined angular distance, such as 12'. Lever bushing 74 is secured to the upper portion of blade drive member 42, as shown, and is provided to engage lever 64. When trigger 46 is in the armed position, i.e., trigger 46 is ready for actuation, lever 64 is biased upward by lever spring 70 so that the upper portion of lever 64 engages lever bushing 74, as shown in FIG. 7.

Figure 8:
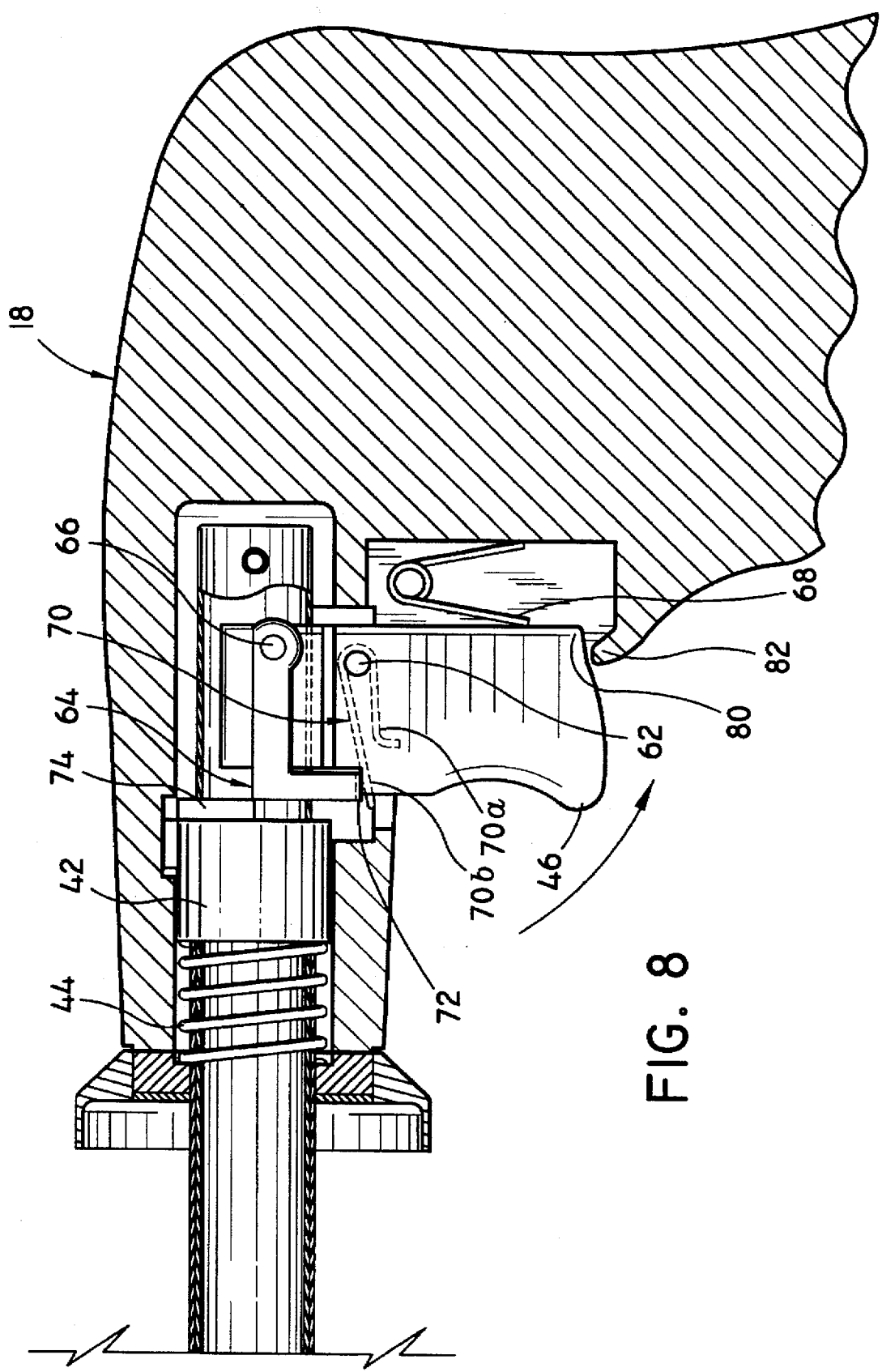

Referring to FIG. 8, actuation of trigger 46, i.e., movement of the trigger in the proximal direction, causes lever 64 to move blade drive member 42 distally to compress drive spring 44 and to advance blade 34 to the deployed position, shown in FIG. 4A. Lever 64 pivots counter-clockwise with the actuation of trigger 46. A tactile or audible indicator may be connected to the actuating assembly 36 to provide a surgeon with an indication that the blade is deployed. For example, trigger 46 may include a camming surface 80 which cams against rib 82 when the trigger is pivoted, as shown in FIGS. 7 and 8. Thus, providing the surgeon with a tactile indication that the blade is deployed.

Figures 9, 10:
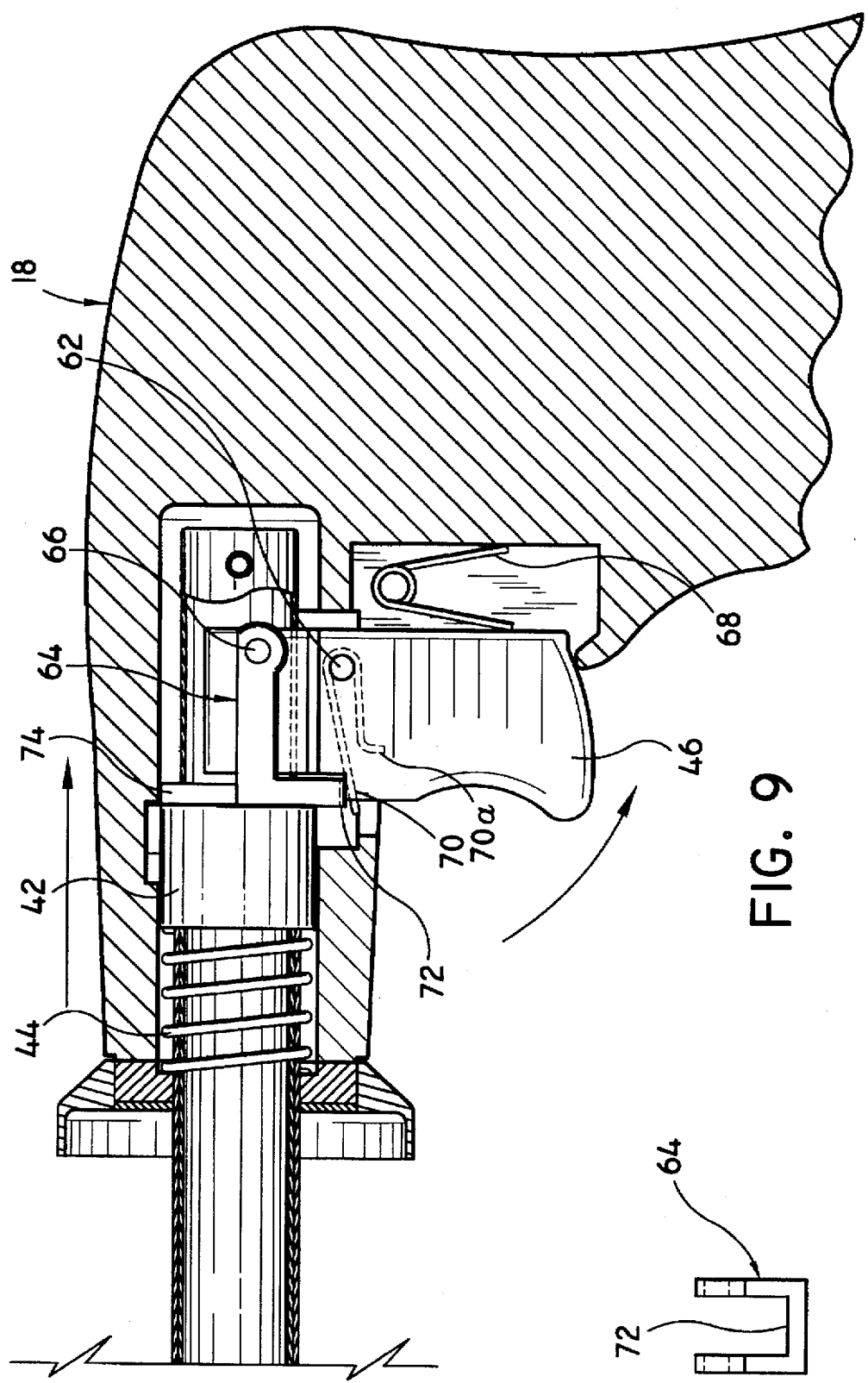
FIG. 10 is a rear plan view of a portion of the automatic release member of the blade actuating mechanism of FIG. 7.

Referring now to FIG. 9, further movement or actuation of trigger 46 in the proximal direction causes lever 64 to continue to pivot counter-clockwise so that the portion of lever 64 engaging lever bushing 74 disengages therefrom. As a result, blade drive member 42 moves proximally under the action of drive spring 44 to move blade 34 to the non-deployed position within blade housing 35, shown in FIG. 3. To re-arm lever 64, trigger 46 is released. Trigger 46 is consequently forced clockwise by spring 68 causing lever 64 to pivot clockwise past bushing 74 as it is pulled slightly proximally by such clockwise movement of trigger 46. When trigger 46 returns to the original, i.e. actuation, position of FIG. 7, lever spring 70 biases lever 64 clockwise to a position which permits engagement with lever bushing 74.

Figures 12, 13:
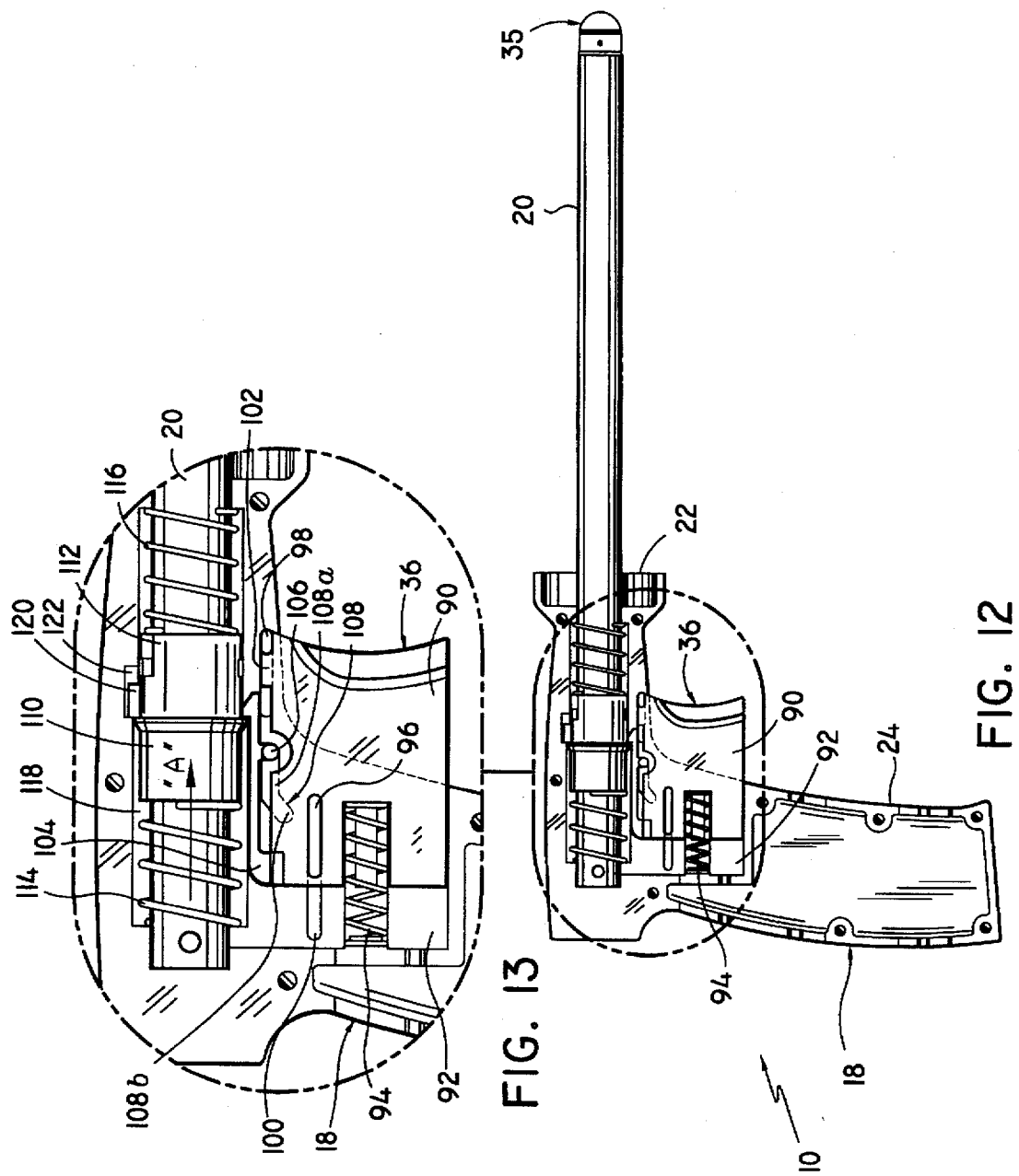
FIG. 12 is a side elevational view of the obturator assembly of FIG. 11.
FIG. 13 is an enlarged side elevational view of the blade actuating mechanism of FIG. 12, illustrating the trigger in a non-actuated position.

Referring now to FIGS. 11, 12 and 13, another alternative embodiment of actuating assembly 36 is shown. This actuating assembly is shown in conjunction with a dome-shaped tip and arcuate blade. However, any of the actuating assemblies can be used with various shaped blades and tips, such as those shown in FIGS. 3B and 3C. In this embodiment of FIGS. 11–13, the actuating assembly 36 includes a trigger 90 slidably positioned within channel 92 in housing 18 and movable between non-actuating and actuating positions. Spring 94 is secured between housing 18 and trigger 90 so as to normally bias the trigger to the non-actuating position, shown in FIG. 12. Alignment fingers 96 and 98 extend from trigger 90 into corresponding channels 100 and 102 within housing 18. Alignment fingers 96 and 98 are provided to maintain the alignment of trigger 90 within channel 92 of housing 18.

Hammer latch 104 is secured to trigger 90 and includes a latch release member, in the form of post 106. Post 106 extends between the two housing halves and into corresponding channel 108 of each housing half, as shown in FIG. 11. Channel 108 include a longitudinal portion 108a which permits the hammer latch 104 to engage the hammer, and a sloped portion 108b which causes hammer latch 104 to disengage from the hammer, as will be described in more detail below.

Referring again to FIGS. 11 and 14, the actuating assembly 36 also includes blade drive members, such as hammer 110, bushing 112 and a pair of drive springs 114 and 116. As shown in FIG. 14, the hammer, bushing and drive springs are coaxially aligned with obturator sleeve 20. Drive spring 114 is positioned about obturator sleeve 20 within channel 118 of each housing half so that one end of the spring engages the housing and the other end engages the proximal end of hammer 110. Drive spring 114 normally biases hammer 110 toward the distal end of the obturator assembly 12, indicated by arrow "A" in FIG. 13. The proximal end of bushing 112 is positioned adjacent hammer 110 and the distal end of bushing 112 engages one end of drive spring 116. The other end of drive spring 116 engages the housing 18, as shown. Finger 120 extending from bushing 112 into channel 122 within housing 18, is provided to limit the proximal and distal movement of the bushing 112 and thus the proximal and distal movement of blade 34.

Referring again to FIGS. 11 and 14, blade pusher arms 124 and 126 are positioned in slots 128 and 130, respectively, within the obturator sleeve 20. The proximal end of each blade pusher arm includes fingers 132 extending outwardly therefrom. Fingers 132 are configured to slide within corresponding notches 134 in bushing 112 to releasably secure the blade pusher arms 124 and 126 to bushing 112, as shown in FIG. 14.

The actuation of actuating assembly 36 is shown in FIGS. 15–20 and described below. Movement of trigger 90 in the proximal direction, shown by arrow "B" in FIGS. 15 and 16, causes hammer latch 104 to retract hammer 110 and compress drive spring 114 (i.e., the hammer latch moves the hammer to a cocked or armed position). Post 106 is within the longitudinal portion 108a of channel 108 and blade 34 continues to remain in the non-deployed (i.e., retracted) position within blade housing 35, as shown in FIG. 17. Further proximal movement of trigger 90 causes post 106 to move in a downward direction within the sloped portion 108b of channel 108, as shown in FIGS. 18 and 19. Downward movement of post 106 causes hammer latch 104 to disengage from hammer 110 so that hammer 110 is thrusted distally (i.e., in the direction of arrow "C") by drive spring 114. As hammer 110 moves distally, the hammer engages bushing 112 and thrusts the bushing distally so as to move blade 34 to the deployed (i.e., exposed) position, shown in FIG. 20. Distal movement of bushing 112 also compress drive spring 116 and when the biasing force of drive spring 116 exceeds the compression force exerted by the hammer 110, drive spring 116 automatically biases bushing 112 proximally so that blade 34 is automatically returned to the non-deployed position. Thus, engagement of hammer 110 and bushing 112 provides substantially instantaneous deployment and retraction of the blade so the blade remains exposed for a short period of time. Thus, once the trigger is pulled to a predetermined position, the blade is deployed and then retracted without further action of the user (i.e., without further movement of the trigger).

In the configuration described, the actuation assembly 36 operates in a two step manner. In the first step, trigger 90 is moved proximally to cock hammer 110. In the second step, further proximal movement of trigger 90 causes the hammer 110 to automatically move distally to advance the blade 34 to the deployed position, and the blade is automatically returned to the non-deployed position under the force of drive spring 116. This two step manner automatically occurs upon fully squeezing the trigger 90. As noted above, a tactile or audible indicator may be connected to the actuating assembly 36 to provide a surgeon with an indication that the blade is deployed.

Referring again to FIG. 1, cannula assembly 14 includes cannula housing 76 and cannula sleeve 78 secured to the cannula housing 76 and extending outwardly therefrom. Obturator housing 18 includes bushing 80 which is configured and dimensioned to interfit with the proximal end of cannula housing 76, so that obturator sleeve 20 coaxially aligns with cannula sleeve 78 when the two assemblies are interfitted. The cannula sleeve 78 is adapted to remain in the body after penetration and subsequent removal of the obturator assembly 12 to allow insertion of appropriate endoscopic and/or laparoscopic instrumentation therethrough.

To maintain a gas tight seal within the cannula housing, a sealing member or system may be positioned therewithin which is adapted to receive the obturator assembly 12, as well as other endoscopic or laparoscopic surgical instruments. One example of a suitable sealing system utilizes a duckbill sealing member. A more detailed description of an exemplary cannula assembly and sealing system is found in U.S. Pat. No. 5,180,373 issued Jan. 19, 1993, which is incorporated herein by reference.

To penetrate body tissue, a surgeon positions the blade housing 35 against the body tissue and continuously moves blade 34 between the non-deployed and deployed positions, i.e., reciprocally moving blade 34 via actuating assembly 36. While reciprocating the blade 34, pressure is applied to hand grip 24 in the distal direction to penetrate the body tissue. The movement of blade 34 facilitates cutting of the body tissue, thus permitting the surgeon to apply relatively minimal pressure to hand grip 24 to penetrate the body tissue.

Once the surgeon penetrates the body tissue, the surgeon releases trigger 46 to permit blade 34 to return to the non-deployed position and discontinues application of pressure to hand grip 24. According to the embodiments of FIGS. 7-10 and 11-20 for the trigger actuating assembly, once the trigger 46 is fully actuated, blade 34 automatically returns to the non-deployed position and release of trigger 46 re-arms the automatic release member.

An alternative method for penetrating the body tissue incorporates blunt penetration for soft tissue and cutting penetration for thicker tissue. For this technique, the surgeon positions the blade housing 35 against body tissue and applies pressure to hand grip 24 to bluntly penetrate soft body tissue. When thicker tissue, such as muscle, is encountered, the blade can be deployed to penetrate (cut through) this thick tissue, then retracted to provide blunt penetration until thick tissue is again encountered, where once again the blade can be deployed.

After penetration into the body cavity, the obturator assembly 12 is removed from the cannula assembly 14, leaving the cannula assembly 14 in the body for insertion of desired instrumentation therethrough.

It will be understood that various modifications can be made to the embodiments herein disclosed without departing from the spirit and scope thereof. For example, various diameters for the cannula assembly, the obturator assembly, as well as various diameter endoscopes are contemplated. Also, various modifications may be made in the configuration of the parts. Therefore, the above description should not be construed as limiting, but merely as exemplifications of preferred embodiments thereof.

What is claimed is:

1. A surgical apparatus comprising:
   a cannula;
   an obturator configured for insertion into the cannula, the obturator having a proximal portion and a distal portion;
   a tissue cutting member mounted to the distal portion of the obturator and movable between deployed and non-deployed positions; and
   an actuating mechanism operatively associated with the tissue cutting member, the actuating mechanism being selectively controllable for moving the tissue cutting member between the deployed and non-deployed positions independent of the position of the obturator;
   wherein movement of the actuating mechanism to a cutting member deployment position causes the cutting member to move to the deployed position, the actuating mechanism at the cutting member deployment position also automatically retracts the cutting member to the non-deployed position, wherein the actuating mechanism cannot maintain the cutting member in the deployed position as each deployment of the cutting member causes automatic retraction of the cutting member.

2. The surgical apparatus according to claim 1, wherein the actuating mechanism includes a trigger operatively associated with the cutting member.

3. The surgical apparatus according to claim 1, wherein the actuating mechanism comprises:
   at least one pusher member having a proximal portion and a distal portion connected to the tissue cutting member, the at least one pusher member being operatively associated with the obturator and longitudinally movable relative thereto;
   a drive mechanism connected to the proximal portion of the at least one pusher member; and
   a trigger operatively connected to the drive mechanism for longitudinally moving the at least one pusher member.

4. The surgical apparatus according to claim 3, wherein the trigger is movable between first and second positions such that movement of the trigger to the first position causes the at least one pusher member to move the tissue cutting member to the deployed position, and causes the at least one pusher member to move the tissue cutting member to the non-deployed position.

5. The surgical apparatus according to claim 1, wherein in the non-deployed position, the tissue cutting member is positioned within a recess in the obturator.

6. The surgical apparatus according to claim 1 further comprising a housing positioned at the distal portion of the obturator and configured to receive the tissue cutting member when in the non-deployed position.

7. The surgical apparatus according to claim 1, wherein the tissue cutting member comprises a blade having an apex.

8. The surgical apparatus according to claim 1, wherein the tissue cutting member comprises an arcuate shaped blade.

9. The surgical apparatus according to claim 1, wherein the cutting member comprises a cutting blade.

10. The surgical apparatus according to claim 9, wherein the actuating mechanism includes a trigger operatively associated with the cutting member.

11. The surgical apparatus according to claim 10, wherein movement of the trigger in a first direction moves the blade to the deployed position and then moves the blade to the non-deployed position.

12. The surgical apparatus according to claim 1, further comprising a first spring for moving a drive hammer in a distal direction to move the cutting member to the deployed position and a second spring for causing movement of the cutting member to the non-deployed position.

13. The surgical apparatus according to claim 12, further comprising a bushing engagable by the drive hammer to move the cutting member to the deployed position, and wherein the second spring moves the bushing proximally to move the cutting member to the non-deployed position.

14. A surgical apparatus comprising:

a cannula;

an obturator configured for insertion into the cannula, the obturator having a proximal portion and a distal portion and defining a longitudinal axis;

a blade mounted adjacent the distal potion of the obturator and extending at an angle with respect to the longitudinal axis of the obturator;

an actuating mechanism having a proximal portion associated with the proximal portion of the obturator and a distal portion operatively connected to the blade, the actuating mechanism configured to move the blade between a retracted position within the distal portion of the obturator and an extended position extending from the obturator wherein movement of the actuating mechanism to a blade deployment position causes the blade to move to the extended position, the actuating mechanism at the blade deployment position also automatically retracts the blade to the retracted position, wherein the actuating mechanism cannot maintain the cutting member in the extended position as each deployment of the cutting member causes automatic retraction of the cutting member.

15. The surgical apparatus according to claim 14, wherein the actuating mechanism is actuable independent of the position of the obturator.

16. The surgical apparatus according to claim 14, wherein the actuating mechanism includes a trigger movable in a first direction to move the blade to the extended position and includes release structure to automatically return the blade to the retracted position.

17. The surgical apparatus according to claim 14, wherein the obturator includes a transverse recess to receive the blade in the retracted position.

18. The surgical apparatus according to claim 17, wherein the blade has two angled edges terminating at an apex.

19. The surgical apparatus according to claim 17, wherein the blade is arcuate in configuration.

20. The surgical apparatus according to claim 14, further comprising first and second longitudinally extending pusher arms operatively connected to the blade and the trigger for moving the blade between the extended and retracted positions.

21. The surgical apparatus according to claim 14, further comprising a first spring for moving a drive hammer in a distal direction to move the blade to the extended position and a second spring for causing movement of the blade to the retracted position.

22. The surgical apparatus according to claim 21, further comprising a bushing engagable by the drive hammer to move the blade to the extended position, and wherein the second spring moves the blade to the retracted position.

* * * * *